US012630482B2

(12) United States Patent
Lew et al.

(10) Patent No.: US 12,630,482 B2
(45) Date of Patent: *May 19, 2026

(54) APPARATUS, SYSTEM AND METHOD FOR AUTOMATED FOOD WASTE PROCESSING

(71) Applicant: Ecotone Renewables PBC, Pittsburgh, PA (US)

(72) Inventors: Dylan Lew, Pittsburgh, PA (US); Eric Darsow, Pittsburgh, PA (US)

(73) Assignee: Ecotone Renewables PBC, Pittsburgh, PA (US)

( * ) Notice: Subject to any disclaimer, the term of this patent is extended or adjusted under 35 U.S.C. 154(b) by 475 days.

This patent is subject to a terminal disclaimer.

(21) Appl. No.: 18/069,933

(22) Filed: Dec. 21, 2022

(65) Prior Publication Data

US 2023/0193177 A1 Jun. 22, 2023

Related U.S. Application Data

(60) Provisional application No. 63/292,450, filed on Dec. 22, 2021.

(51) Int. Cl.
  *C05F 9/02* (2006.01)
  *B07C 5/342* (2006.01)
  (Continued)

(52) U.S. Cl.
  CPC .............. *C05F 9/02* (2013.01); *B07C 5/3422* (2013.01); *B09B 3/35* (2022.01); *B09B 3/65* (2022.01);
  (Continued)

(58) Field of Classification Search
  CPC ............ B07C 5/34; B07C 5/3422; C05F 9/02
  (Continued)

(56) References Cited

U.S. PATENT DOCUMENTS 5,806,759 A * 9/1998 Axisa ...................... B65F 1/004
                                                    193/34
8,662,791 B2 3/2014 Allen et al.
  (Continued)

FOREIGN PATENT DOCUMENTS

AU      2021201990 A1 * 4/2021 ............. G06Q 10/30
WO   WO-2022170273 A1 * 8/2022 ............. G06N 3/042

OTHER PUBLICATIONS

Adedeji et al., "Intelligent Waste Classification System Using Deep Learning Convolutional Neural Network," 2nd International Conference on Sustainable Materials Processing and Manufacturing, 2019, 607-612, ScienceDirect.
(Continued)

*Primary Examiner* — Terrell H Matthews
(74) *Attorney, Agent, or Firm* — Build IP, LLC; Robert V. Donahoe

(57) ABSTRACT

An automated food waste processing system including an enclosure secured to prevent unauthorized access to contents contained therein, the enclosure including a plurality of exterior walls and a food waste processing system housed within the enclosure. The food waste processing system including an imaging system configured to capture a plurality of images of the food waste and the non-biodegradable material received by the sorting receptacle, a processing system configured to process the plurality of images using a trained neural network to identify at least plastic waste and metal waste as the non-biodegradable material when included in the food waste input stream as received by the sorting receptacle, and a sorting system configured to, in response to instructions received from the processing system, automatically locate and remove the non-biodegradable material from the sorting receptacle to create a bio-degradable input stream to the anaerobic digester.

13 Claims, 7 Drawing Sheets

(51) Int. Cl.

| | |
|---|---|
| *B09B 3/35* | (2022.01) |
| *B09B 3/65* | (2022.01) |
| *C02F 1/00* | (2023.01) |
| *C02F 11/04* | (2006.01) |
| *C05F 17/70* | (2020.01) |
| *C05F 17/971* | (2020.01) |
| *C05F 17/993* | (2020.01) |
| *C05G 5/20* | (2020.01) |
| *C12M 1/107* | (2006.01) |
| *G01N 33/02* | (2006.01) |
| *G06T 1/00* | (2006.01) |
| *G06V 10/82* | (2022.01) |
| *G06V 20/60* | (2022.01) |
| *B09B 101/70* | (2022.01) |
| *C02F 103/32* | (2006.01) |

(52) U.S. Cl.
CPC .............. *C02F 1/008* (2013.01); *C02F 11/04* (2013.01); *C05F 17/70* (2020.01); *C05F 17/971* (2020.01); *C05F 17/993* (2020.01); *C05G 5/20* (2020.02); *C12M 21/04* (2013.01); *G01N 33/02* (2013.01); *G06T 1/0014* (2013.01); *G06V 10/82* (2022.01); *G06V 20/60* (2022.01); *B07C 2501/0054* (2013.01); *B07C 2501/0081* (2013.01); *B09B 2101/70* (2022.01); *C02F 2103/32* (2013.01); *C02F 2201/005* (2013.01); *C02F 2209/005* (2013.01)

(58) Field of Classification Search
USPC ........................................................ 209/577
See application file for complete search history.

(56) References Cited

U.S. PATENT DOCUMENTS

| | | | |
|---|---|---|---|
| 9,879,285 | B2 | 1/2018 | De Lima Vasconcellos et al. |
| 10,669,521 | B2 | 6/2020 | Allen et al. |
| 11,069,053 | B2 | 7/2021 | Horowitz et al. |
| 11,135,620 | B2 | 10/2021 | Parr |
| 12,180,127 | B2 | 12/2024 | Lew et al. |

| | | | | |
|---|---|---|---|---|
| 2005/0126958 | A1 | 6/2005 | Bohlig et al. | |
| 2006/0151497 | A1 | 7/2006 | Underwood | |
| 2007/0029232 | A1 | 2/2007 | Cowling et al. | |
| 2010/0206791 | A1 | 8/2010 | Lee et al. | |
| 2012/0064562 | A1 | 3/2012 | Allen et al. | |
| 2014/0134694 | A1* | 5/2014 | Gitschel | C10L 3/106 435/267 |
| 2014/0147911 | A1 | 5/2014 | Allen et al. | |
| 2014/0273199 | A1* | 9/2014 | Cole | C07C 29/1518 435/297.2 |
| 2015/0209978 | A1 | 7/2015 | Snyder et al. | |
| 2016/0159572 | A1 | 6/2016 | Prewett | |
| 2018/0030399 | A1 | 2/2018 | Allen et al. | |
| 2020/0034785 | A1* | 1/2020 | Romano | G06N 3/0464 |
| 2020/0050922 | A1* | 2/2020 | Wu | G06N 3/045 |
| 2023/0011695 | A1* | 1/2023 | Gentry | B65F 3/22 |
| 2023/0192571 | A1 | 6/2023 | Lew et al. | |
| 2023/0193177 | A1* | 6/2023 | Lew | C05F 17/993 435/41 |

OTHER PUBLICATIONS

Liu et al., "Exploring features in a Bayesian framework for material recognition," Proceedings of the IEEE Computer Society Conference on Computer Vision and Pattern Recognition, 2010, 239-246, MIT Open Access Articles.

Donovan, "Auto-Trash sorts garbage automatically at the TechCrunch Disrupt Hackathon," 2016, TechCrunch, available at https://techcrunch.com/2016/09/13/auto-trash-sorts-garbage-automatically-at-the-techcrunch-disrupt-hackathon/.

Batinic et al., "Using ANN model to determine future waste characteristic in order to achieve specific waste management targets—case study of Serbia," Journal of Scientific & Industrial Research, 2011, pp. 513-518, vol. 70.

Mittal et al., "SpotGarbage: Smartphone App to Detect Garbage Using Deep Learning," UbiComp '16, 2016, pp. 940-945, Heidelberg, Germany.

Thung et al., "Classification of Recyclability Status," 2016, 940-945, Stanford University.

International Search Report and Written Opinion, dated Mar. 16, 2023, for corresponding International Application No. PCT/US2022/082161.

* cited by examiner

APPARATUS, SYSTEM AND METHOD FOR AUTOMATED FOOD WASTE PROCESSING

BACKGROUND OF INVENTION

1. Field of Invention

This invention relates generally to the anaerobic digestion of food waste. More specifically, at least one embodiment, relates to a smart food waste processing system that employs artificial intelligence to automate a conversion of food waste into fertilizer and energy

2. Discussion of Related Art

Food waste is a very expensive problem in the developed world, particularly in the US where the annual cost of food waste is hundreds of millions of dollars. Food waste also directly harms the environment because rotting food contributes to the emission of greenhouse gas. As a result, many types of recycling and waste recovery systems have been implemented. One such approach is the use of anaerobic digestion to convert food waste into useful byproducts such as liquid fertilizer and biogas. The fertilizer can be used to fertilize agricultural crops while the biogas can be used as fuel for heating systems, electrical generators, combustion engines, and fuel cells. However, anaerobic digestion is typically provided on an industrial scale at large plants. These plants cost millions of dollars to permit and construct. In addition, they involve high waste hauling costs and substantial CO2 emissions generated by the waste haulers who transport waste to the plant. These large-scale plants also become a significant source of odors and pests which makes the plants more difficult to site. Further, even when these facilities are successfully launched, the nature of food waste streams means that the food waste input into the system must be screened for non-biodegradable contaminants.

Prior art approaches to waste separation include manual separation that requires individuals stand proximate the waste stream and selectively identify and remove non-recyclable material by hand. These approaches can also include a similar process in which different types of recyclable materials are manually identified and then selectively separated from one another. For example, glass bottles can be separated from plastic bottles. Current single stream recycling approaches can also include imaging systems that process images of the waste stream for an identification of the different categories of recycled materials that must be separated and directed into different recycling waste streams.

Some prior approaches employ a neural network to distinguish different types of food waste materials, for example, see U.S. Pat. No. 11,069,053 entitled "Systems and Methods for Optical Material Characterization of Waste Materials Using Machine Learning." However, these approaches simply characterize materials within the family of food waste, for example, to distinguish the different food waste materials to estimate the energy that will be supplied for anaerobic digestion. These prior approaches do not distinguish between biodegradable material suitable for anaerobic digestion and non-biodegradable material found in the waste stream which is unsuitable for anaerobic digestion. Consequently, these systems are not automated at least because current approaches for waste screening do not properly address the screening required to identify the variety of non-biodegradable material that may be found in a food waste stream. Further, current anaerobic digestion systems are not designed for operation independent of electrical grids and external sources of water. Thus, current anaerobic digester systems cannot be provided as autonomous, self-contained modular systems.

Additionally, current approaches apply image systems to categorize an item that is a single item in the image. However, these systems cannot categorize an item when the images include multiple items. These approaches cannot be employed with food waste because images of food waste include multiple different items in close contact with one another. Further, there is no prior approach that can detect both metal and plastic in a food waste stream when it can include both types of contamination.

SUMMARY OF INVENTION

Therefore, there is a need for apparatus, systems and methods that automate the process of identifying non-biodegradable material in a food waste stream and then automatically remove the non-biodegradable material. There is also a need for distributed anaerobic digestion systems placed at the sources of food waste such as restaurants, grocery stores, and apartment buildings. According to some embodiments, modular food waste processing systems operate in an automated fashion to allow restaurant staff, grocery store staff, pedestrians, or other personnel untrained in the operation of the anaerobic digester system to safely place food waste at an input to the anaerobic digestion system. These untrained personnel can then walk away while the system operates in an automated mode to effectively process the food waste after the removal of the non-biodegradable material by the system. Various embodiments automatically identify, separate, and remove non-biodegradable material from the food waste stream. This can eliminate pump and pipe clogging, remove microplastics, prevent grinding equipment damage, bacteria microbiome damage, and sedimentation that can occur in an anaerobic digestion system.

In various embodiments, these system produce useful outputs in the form of liquid fertilizer and biogas. The liquid fertilizer effectively captures nutrients contained in the food waste that would otherwise be lost. In further embodiments, the biogas is used as fuel for any of a hot water heater, a heating system, combustion engine, fuel cell, and an electrical generator.

According to some embodiments, the modular anaerobic digestion systems are entirely independent of the electrical grid and any outside source of water. The electrical systems of these independent, self-contained anaerobic digester systems can include batteries to store excess energy produced by the integral biogas powered electrical generator. They can also include integral solar panels, solar water heaters, fuel cells, and/or micro wind turbines to increase the overall electrical generating capability of the system. The energy efficiency of the overall system can also be improved with increased insulation of the housing that encloses the system and increased insulation of process equipment and process piping. Depending on the embodiment, independence in relation to the source of water can be achieved through rainwater collection, an on-site well with electrically driven pump, integral air moisture capture technology, micro-desalination, or other apparatus. According to various ones of the preceding embodiments, the anerobic digestion system is a stand-alone unit with no need for external electrical connections or external water-line connections.

According to various embodiments, apparatus, systems and methods include a convolutional neural network employed to analyze images of a food waste stream to automatically identify the non-biodegradable material included in the waste stream. According to these embodiments, a separation system operates in combination with the image-analysis system to automatically separate the non-biodegradable material from the food waste stream. These embodiments can be employed to improve the operation of a waste processing system including an anaerobic digester.

According to one aspect, an automated food waste processing system includes an enclosure secured to prevent unauthorized access to contents contained therein, the enclosure including a plurality of exterior walls and a food waste processing system housed within the enclosure. In some embodiments, the food waste processing system includes an anaerobic digester, a sorting receptacle configured to receive a food waste input stream for the anaerobic digester, an imaging system configured to capture a plurality of images of the food waste and the non-biodegradable material received by the sorting receptacle, a processing system configured to process the plurality of images using a trained neural network, a sorting system configured to, in response to instructions received from the processing system, automatically locate and remove the non-biodegradable material from the sorting receptacle to create a bio-degradable input stream to the anaerobic digester; and a port coupled to the sorting receptacle. In some embodiments, the processing system using the trained neural network operates to identify at least plastic waste and metal waste as the non-biodegradable material when included in the food waste input stream as received by the sorting receptacle. In further embodiments, the port is accessible at an outside surface of an exterior wall included in the plurality of exterior walls, the port configured to allow personnel untrained in an operation of the food waste processing system to deposit the food waste input stream from a location outside of the enclosure.

According to another aspect, an automated food waste processing system includes a sensor array included in an anaerobic digester, a dosing tank with an input coupled to a sorting system and an output coupled to an input of the anaerobic digester, a pump including an input and an output, a plurality of electrically operated valves coupled to a processing system, a food waste disposal unit including an input coupled to the sorting system and an output coupled to the input of the pump via a first electrically operated isolation valve included in the plurality of electrically operated valves, a second electrically operated isolation valve included in the plurality of electrically operated valves and coupled to the output of the dosing tank and the input of the pump, a third electrically operated isolation valve included in the plurality of electrically operated valves and coupled to the input of the anaerobic digester and the output of the pump, a fourth electrically operated isolation valve coupled to the output of the anaerobic digester and the input of the pump; and a fifth electrically operated isolation valve coupled to the input of the fertilizer tank and the output of the pump. According to some embodiments, the pump is configured to move the bio-degradable input stream through the automated food waste processing system and the food waste disposal configured to process the bio-degradable input stream supplied to the dosing tank. In further embodiments, the processing system is configured to automatically control an operation of the plurality of electrically operated valves to circulate the biodegradable input stream and the liquid fertilizer based on a status of a digestion process being performed by the anaerobic digester where the status is determined using information provided by the sensor array.

According to another aspect, a method of sorting a food waste input stream to generate an input stream to an anaerobic digester is provided. According to some embodiments, the method includes receiving a food waste input stream that includes a 95% or greater percentage by weight of biodegradable food waste, automatically processing images of the food waste input stream to identify non-biodegradable waste including identifying plastic waste and metal waste included in the food waste input stream, automatically sorting the food waste input stream to remove the plastic waste and the metal waste based on information provided by the processing of the images and automatically delivering the sorted food waste input stream to the anaerobic digester. According to some embodiments, the method automatically maintains the food waste input stream in a first location for sorting for a predetermined amount of time, performs a series of automated sorting operations to displace the food waste within the first location, captures an image of the food waste input stream before the food waste is displaced; and captures an image of the food waste input stream after it is displaced. A plurality of displacement operations are performed using robotic arm and a plurality of images captured. The images are processed with a convolution neural network.

According to still another aspect, a system for identification and separation of non-biodegradable material from a food waste input stream includes a sorting receptacle configured to receive a food waste input stream including food waste and non-biodegradable material, an imaging system configured to capture a plurality of images of the food waste and the non-biodegradable material received by the sorting receptacle, a processing system configured to process the plurality of images using a convolutional neural network to identify at least plastic waste and metal waste as the non-biodegradable material when included in the food waste input stream as received by the sorting receptacle and a sorting system configured to, in response to instructions received from the processing system, locate and remove the non-biodegradable material from the sorting receptacle to create a bio-degradable input stream suitable for processing further as an input to an anaerobic digester.

As described herein, the term "biodegradable" refers to materials that are capable of being decomposed by bacteria or other living organisms. Those of ordinary skill in the art will recognize in view of the disclosure herein that food waste, beverage waste, oil waste, yard debris, paper, and compostable products are biodegradable. One of ordinary skill in the art will also recognize that other materials such as steel, glass, and plastic that eventually breakdown are not biodegradable as the term is used herein.

As used herein, the term "automatic" or "automated" when used in reference to an operation of a waste sorting system refers to an operation that occurs without any real-time control or intervention by a human operator. Those of ordinary skill in the art will recognize based on the disclosure herein that a food waste processing system that operates to do any of the following sorting, grinding, and adding material to an anaerobic digester without any real-time control or intervention by a human operator is an automated system. Those of ordinary skill in the art will further recognize based on the disclosure herein that the preceding system is automatic even where the system receives food provided manually by users at a waste input receptacle.

As used herein, the term "food waste input stream" means an input stream that contains 50% or greater biodegradable material by weight. One of ordinary skill in the art will recognize that trash and garbage are distinguished from a food waste input stream because trash and garbage are mixed waste streams that can include widely varying amounts of non-biodegradable materials including 50% or greater non-biodegradable material by weight. For example, the EPA estimates that the trash that is landfilled in the U.S. includes 24% food with the remaining 76% other forms of solid waste.

Applicant finds that food waste processing systems can be provided with much higher percentages of biodegradable material by weight if the food waste input stream is pre-screened. In these embodiments, the waste generators properly segregate material as it is admitted into the waste stream. For example, a restaurant may provide employees with the education, training and tools that allow them to segregate food waste from other waste material when they place it in containers at the restaurant. The material in the food waste receptacles is then provided as the input to the food waste processing system. As used herein, a "pre-screened food waste input stream" means an input stream that contains 95% or greater biodegradable material by weight.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
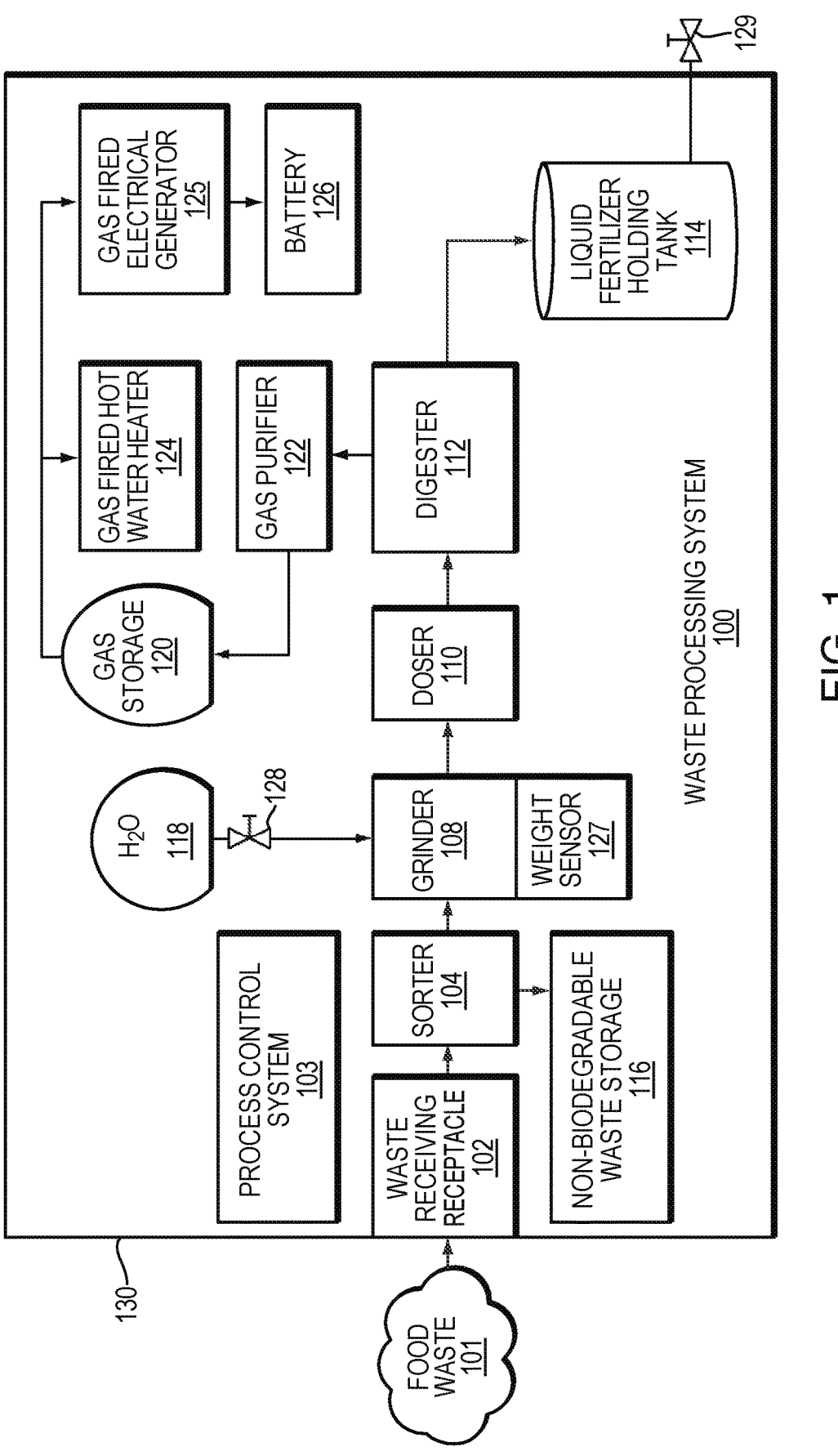
FIG. 1 illustrates a system level block diagram of a waste processing system in accordance with one embodiment.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Referring to FIG. 1, a waste processing system 100 is illustrated in accordance with one embodiment. In various embodiments, the waste processing system 100 operates with food waste 101, for example, to create liquid fertilizer and biogas. According to the illustrated embodiment, the waste processing system 100 includes a waste receiving receptacle 102, a process control system 103, a waste sorter 104, a waste grinder 108, a doser 110, a digester 112 and a liquid fertilizer holding tank 114. The waste processing system 100 also includes a non-biodegradable waste receiver 116, a water source 118, a gas storage vessel 120, a gas purifier 122, a gas hot water heater 124, a gas fired electrical generator 125 and a battery 126. According to various embodiments, the waste processing system 100 is self-contained within an overall housing 130. For example, the system 100 can be housed in a refitted shipping container.

The waste processing system 100 can include a variety of components to facilitate operation including automated operation of the system 100. According to the illustrated embodiment, the waste processing system 100 includes a weight sensor 127, a first control valve 128 and a second control valve 129. As is described in detail below, the waste processing system 100 can include additional valves, additional sensors, pumps, and other process monitoring and control components that allow the waste processing system 100 to operate in an automated manner. According to these embodiments, automated operation eliminates the need for an operator to be present during the waste inputting, waste sorting, waste grinding, anaerobic digester dosing, digesting and fertilizer dispensing operations. Instead, these and other operations described herein need only be checked periodically by qualified personnel.

According to various embodiments, the waste processing system 100 is provided in a self-contained modular enclosure with various features that provide a substantially automated operation. For example, the waste receiving receptacle 102 can provide an input accessible from the exterior of the enclosure to allow pedestrians or food industry workers to place food waste easily and safely into the waste processing system 100 while the system is operating. Depending on the embodiment, the waste receiving receptacle 102 can include any of a chute, a latching lid, a drawer, a rolling drawer, a tube, a window, a ramp, a drop box, a conveyor belt, a bin or a bucket either alone or in combination with one or more of the preceding mechanical designs or other features. According to one embodiment, the waste receiving receptacle includes a spring loaded, hinged outer door that is pulled open by the user to provide access to a chute. The chute provides a gravity feed for the food waste from the outer door to the sorter 104.

The sorter 104 is used to remove non-biodegradable waste from the waste stream. According to some embodiments, the sorter operates to both detect foreign objects in the waste stream (for example, material that is not suited for anaerobic digestion) and to separate those foreign objects from the biodegradable waste. This approach increases the efficiency and reliability of operation of the digester 112. In various embodiments, one or more cameras and an associated lighting system are employed to illuminate the waste stream and capture images and/or video of the waste stream. The image stream is processed with an image processing algorithm using machine learning. According to one embodiment, the program includes a convolutional neural network program or similar visual machine learning program to categorize waste and identify non-biodegradable objects included in the food waste stream. According to various embodiments, a computer or other processing system, for example, a Raspberry Pi is employed to run the program. In various embodiments, the processing system is in communication with remote resources via a wireless network that may include cellular networks, Wi-Fi and/or the Internet. According to these embodiments, the machine learning program can be downloaded to the processing system via the wireless network. The image processing algorithm, for example, including the convolutional neural network and associated processing system are included in the process control system 103.

Depending on the embodiment, the sorter 112 can include a conveyor or simply a gravity feed system to move food waste from the waste receiving receptacle 102 to the grinder 108. The sorting can be accomplished using any of magnets, electromagnets, eddy current separators either alone or in combination to remove metals from the waste stream. The sorter 104 can also include any of robotic arms, a density separator, a latch-activated drop platform, a tilting table, or sifters either alone or in combination to remove individual non-biodegradable objects or batches of food waste in which a non-biodegradable object is detected. According to the illustrated embodiment, the sorter includes non-biodegradable waste storage 116 that receives the non-biodegradable waste that is identified and removed in the sorting process.

The grinder 108 is used to reduce the size of the solids included in the waste stream before they are provided to the doser 110 and digester 112. Depending on the embodiment, the grinder 108 can include a food processor, a blender, a grinder, a grind pump, or other grinding and mixing device. According to various embodiments, the waste processing system 100 operates such that operation of the grinder 108 is substantially automatic. This is accomplished by automating both the water input to the grinder 108 and operation of the grinder 108 itself. The preceding can permit operation of the grinder without the need for a technician to be present. According to one embodiment, the grinder 108 includes the weight activated sensor 127. For example, the sensor 127 can determine a measured weight in the manner of a scale. In another embodiment, the sensor 127 can determine a liquid level in the grinder and calculate the weight of the material in the grinder 108 based on the calculated volume of the material and a material density. The material density can either be measured or estimated depending on the embodiment. According to one embodiment, an output of the weight sensor 127 (for example, a change of state of an electrical contact) is used to operate the grinder 110 to initiate a grinding, blending, pumping, mixing or other operation performed by the grinder 110. According to other embodiments, the output of the weight sensor 127 is provided to the process control system 103 which then initiates any of the preceding operations of the grinder 108 based on the sensed weight alone or in combination with other system parameters.

Water is added to the biodegradable waste received by the grinder 108 to provide a food waste output suitable for processing in the digester 112. According to the illustrated embodiment, the water source 118 provides the source of water for the waste processing system 100. According to embodiments where the waste processing system 100 is a self-contained operating system the water source 118 includes a holding tank with sufficient capacity for system operation for a known interval. According to other embodiments, the water source 118 is plumbed to a source of city water or well water. In either approach, an operation of the first control valve 128 is controlled to automatically feed water into the grinder 108 as needed. According to one embodiment, this determination is based on the sensed weight as provided by the weight sensor 127 either alone or in combination with other system parameters. Further, the process control system 103 can respond to the status of the operations performed by the grinder 108 to automatically recycle and pump food waste processed in the grinder 108 to the doser 110. As will be apparent to those of skill in the art in view of the disclosure provided herein, the waste processing system 100 can include one or more pumps to move the processed food waste (for example, a food waste slurry) to the doser 110.

The doser 110 operates to move known amounts of food waste slurry into the digester 112. Here too, operation of one or more pumps or grind pumps is initiated by the process control system 103 to control the timing and amount of material provided to the digester 112 based on a timer and/or feedback provided by sensors included in the waste processing system 100. For example, separate liquid level sensors can provide information on the liquid levels in the doser and the digester, respectively. The process control system 103 can operate to adjust the run times and frequency of operation of one or more pumps that feed material from the output of the doser 110 to the digester 112 based on sensed tank levels either alone or in combination with other system parameters. According to one embodiment, an on/off timer to control pump operation is connected to a Wi-Fi or a cellular signal and can transmit and change operating parameters based on wireless commands from operating-side of mobile application included in the process control system 103. In various embodiments, the preceding operations are automatically controlled by the control system to reduce the frequency at which system operation must be checked on-site by an operator.

According to one embodiment, the digester 112 is an anaerobic digester that operates to break down food waste in the absence of oxygen. In various embodiments, the digester 112 includes a sealed vessel (referred to as "a reactor") that receives the food waste slurry from the doser and generates an output of biogas and digestate in the form of liquid fertilizer that are discharged from the digester 112.

According to one embodiment, the liquid fertilizer holding tank 114 includes a cylindrical, cone-shaped tank that prevents sedimentation and clogging of liquid fertilizer lines. Another embodiment uses a rectangular holding tank 114 with a mixing pump at the bottom to prevent sedimentation. An accessible faucet can be provided outside of the housing 130 for dispensing liquid fertilizer. According to one embodiment, the faucet is located at the outlet side of the second control valve 129. The second control valve 129 can include an automated valve whose operation is controlled by the process control system 103. For example, the second control valve 129 can be controlled to open and close to release a specified quantity of fertilizer. For example, the second control valve 129 can be controlled to dispense a predetermined amount of liquid fertilizer to fill a container having a known volume. In some embodiments, an end user can employ a mobile app on their own electronic device (for example, phone or tablet) in combination with the waste processing system 100 to control an operation of the second control valve 129. This can allow consumers to scan a QR code or enter a code to activate the second control valve 129 and receive liquid fertilizer dispensed from the liquid holding tank 114 via the valve.

The gas purifier 122 receives the biogas discharged from the digester 112 and operates to purify and improve the characteristics of the gas to allow its use in a variety of different applications. In general, the gas purifier 122 captures smelly and energy-dense gasses, scrubs them to remove sulfur, and produces clean and odor-free renewable energy. In various embodiments, the gas purifier operates as a gas scrubber to remove water vapor, hydrogen sulfide and carbon dioxide from the biogas. For example, the gas purifier 122 can employ any one of or combination of condensation, adsorption through silicon dioxide, filtration through activated carbon or molecular sieves, and absorption through glycol solutions or hygroscopic salts to remove water. Similarly, the gas purifier 122 can employ any one of or combination of precipitation with iron ions and adsorption using activated carbon too remove hydrogen sulfide. For the removal of carbon dioxide, the gas purifier 122 can employ any one of or combination of water scrubbing, membranes, cryogenic upgrading, or other biogas upgrading techniques.

In various embodiments, the gas storage 120 includes a sealed tank or bladder with sufficient capacity to store the biogas discharged from the digester 112 after it is treated using the gas purifier 122. The gas can be stored for a variety of uses including the generation of electricity, heating, water heating and as fuel for vehicles that operate on CNG.

According to the illustrated embodiment, the waste processing system 100 includes both the gas fired hot water heater 124 and the gas fired electrical generator 125. The treated biogas is supplied as fuel to the gas fired hot water heater 124. According to some embodiments, the gas fired hot water heater 124 operates to heat hot water that is used by the waste processing system 100, for example, as water added to the food waste stream. The gas fired electrical generator 125 employs natural gas to drive an electrical generator to output electricity. In various embodiments, the electricity can be used to operate equipment included in the waste processing system 100. The electricity can also be supplied back to the local electrical grid. According to the illustrated embodiment, electricity output by the gas fired electrical generator is stored in the battery 126. For example, the battery 126 can be included in the waste processing system 100 in combination with an inverter to provide a source of electricity regardless of the operational status of any other integral sources of power included in the system 100 or electrical grid.

The waste processing system can also include a green energy vehicle fueling station. According to one example, the battery 126 can be connected to an EV charging station accessible at an exterior of the housing 130. The gas stored in the gas storage vessel 120 can also be provide at a CNG-vehicle fueling station accessible at an exterior of the housing 130 to fuel gas-powered vehicles.

In various embodiments, the process control system 103 operates monitor and control the operation of the components of the waste processing system 100. These operations can include, for example, operations that move food waste from the waste receiving receptacle 102 to the sorter 104, operation of the sorter 104 to separate non-biodegradable material from the waste stream, operation of the grinder 108 to grind and liquefy the waste stream, operation of the doser 110 to periodically add the correct amount of food waste to the digester 112 and operation of the digester 112 to convert the food waste to liquid fertilizer and deliver the fertilizer to the holding tank 114. The operation of the gas purifying system, gas storage and related equipment are also controlled by the process control system 103 in accordance with some embodiments. Depending on the embodiment, the process control system 103 includes a computing device such as a general purpose computer such as a PC, a laptop, a tablet computer or other computing device. According to one embodiment, the process control system 103 includes a RASPBERRY PI brand minicomputer. Depending on the embodiment, the process control system 103 can be provided as a centralized system or include various elements distributed within the housing 130. For example, a processing system such as a PC or tablet computer can be combined with distributed processing elements such as minicomputers that provide functionality in a specific process control area.

The process control system 103 can include a network interface suitable for wired or wireless communication with either or both of local equipment and remote resources. In one embodiment, the remote resources are hosted on one or more servers geographically remote from the waste processing system 100. For example, in one embodiment, the network interface is suitable for communication with a remote cloud connected system that can provide the algorithms employed with an image processing system included in the waste processing system 100. As described with reference to FIG. 2, the image processing system can employ the convolutional neural network to screen the waste stream for non-biodegradable items.

The communication capabilities provided with the process control system 103 can allow software updates to be pushed to the control system 103 to improve system operations. For example, accuracy of the neural network can be improved by training the model with additional data that is captured during operation of the system 100. In some embodiments, users can also communicate with the process control system 103 via a mobile application. According to some embodiments where the user is proximate the waste processing system 100, Wi-Fi is employed to communicate information between the mobile app on the user's phone and the system 100. In other embodiments, the mobile app allows the user to communicate with remote cloud-based resources. The cloud-based resources can communicate with the process control system 103 to provide software updates, monitor system status and control operation of the waste processing system 100. According to various embodiments, the remote monitoring and control are performed automatically, for example, to optimize system operation for the then current circumstances.

As mentioned above, various embodiments can include a neural network program to classify food waste that is input to the waste processing system 100. These embodiments can operate to categorize the food waste into either of two categories. Category 1 is food waste that is acceptable for processing by the waste treatment system 100. Category 2 is food waste that is not acceptable for processing by the waste treatment system 100. According to some embodiments, category 1 is biodegradable waste and category 2 is non-biodegradable waste. In operation, the waste processing system 100 removes the nonbiodegradable waste from the waste stream when category 2 waste is identified by the image processing system.

Additionally, these embodiments can include data collection and processing for the type of biodegradable material and food waste being processed. This can be used to highlight largely wasted items to further reduce these items being wasted in future inputs. According to one embodiment, the data collection includes keeping track of the number of each type of wasted fruit and vegetable. This is then reported to the system user to reduce future purchases of those largely wasted items.

According to one embodiment, the waste identification algorithm is developed and trained using APIs including TensorFlow for image pattern recognition, NumPy for mathematical calculations, Matplot for plots and graphs, and Pandas for reading, organizing, and sorting data. An initial image set is selected for training where the image set includes waste detection images. In one embodiment, the Kaggle platform is used to manage the data set for training and testing. The machine learning process includes resizing images from the training data set, inputting a feature map into the model, passing the model through stacked convolution and max pooling layers and training the model using binary cross entropy.

The image processing system is set up to detect images and run the program. According to one embodiment, the program is cloned from a remote directory (for example, GitHub) for operation by a processing system included in the waste processing system 100. According to various embodiments, the convolutional neural network program operates continuously or in batches to process images that are provided by the imaging system.

According to one embodiment, the convolutional neural network program trained via machine learning achieves a minimum accuracy of 90% for foreign object detection. That is, detection of non-biodegradable objects in the waste stream. In some embodiments, accuracy is further improved by training the system with additional training data collected during actual operation of the waste processing system 100.

According to another embodiment, a waste classification algorithm employs a VGG16 convolutional neural network model trained using supervised machine learning to process images of the waste stream and distinguish between organic and inorganic waste. The process can be implemented using a support vector machine coded in the Python programming language. According to one embodiment, Jupyter Notebooks is employed to write the code which is then converted to regular Python. The overall approach establishes a set of feature vectors that are trained using a set of waste classification images that are divided into a training set and a validation set. According to one embodiment, the training is performed to not only identify non-biodegradable waste, but to also identify food waste that is biodegradable but still not desired for use with the anaerobic digester. Stated differently, the convolutional neural network can screen the food waste for unacceptable biodegradable material. Examples of materials that are biodegradable but nonetheless may be separated from the material fed to the anaerobic digester include salty foods, tree branches and oyster shells. This material can be separated from the food waste by the sorter 104. The removal of these various types of waste can improve system operation and/or the qualities of fertilizer that is produced by the system (for example, by removal of the salty foods).

The process continues with the generation of the code that performs the image processing during operation of the waste processing system 100. According to some embodiments, these files include algorithms that segment the images of the food waste stream before processing them using the classification algorithm with convolutional neural network. According to one embodiment, the image processing files are downloaded to the process control system 103.

Figure 2:
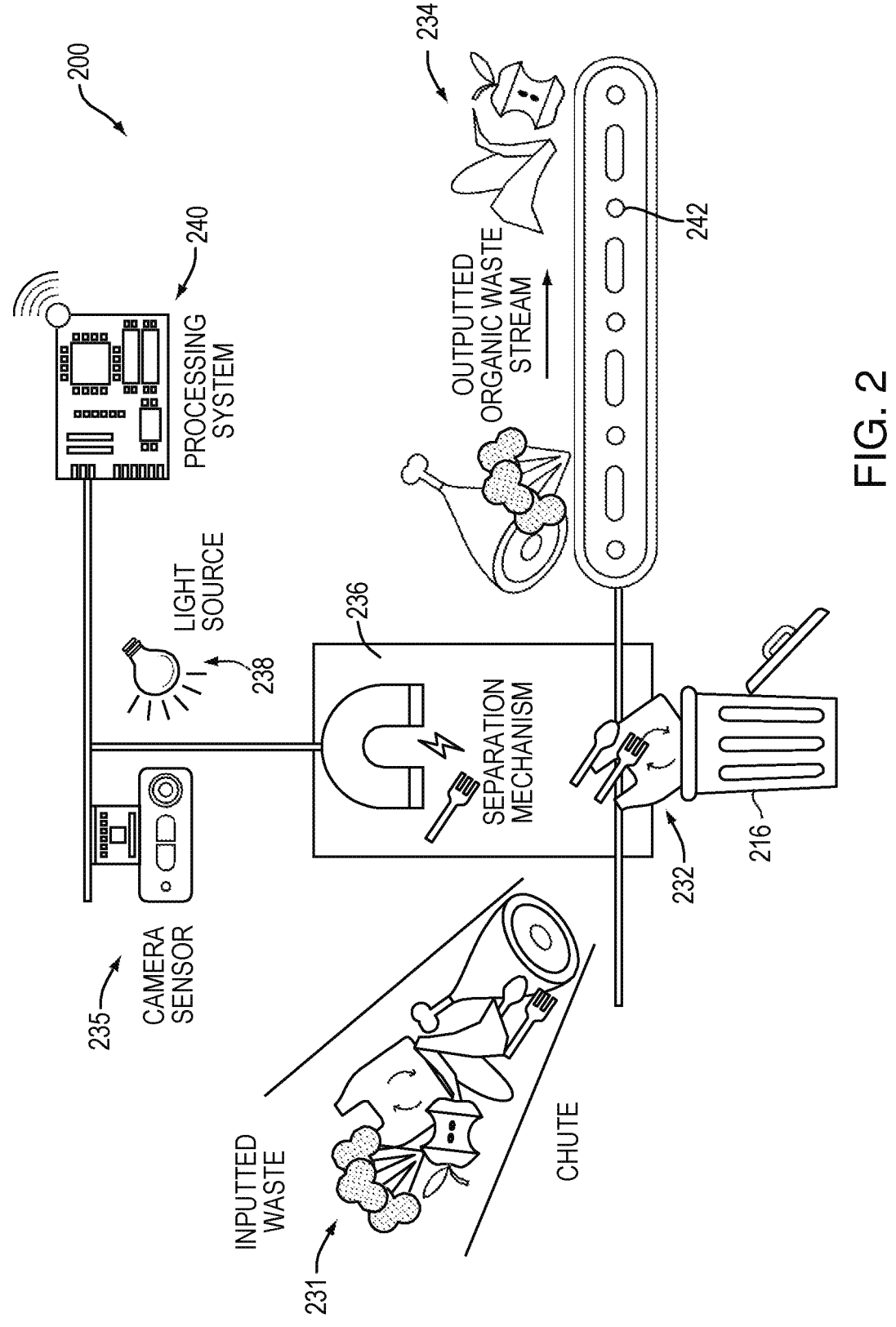
FIG. 2 illustrates elements of a system for waste detection and separation in accordance with one embodiment.

Referring now to FIG. 2, a foreign object detection and separation system 200 is illustrated in accordance with one embodiment. In various embodiments, the system 200 employs an artificial intelligence engine for image processing to identify and remove non-biodegradable material from the food waste 101 that is received and processed by the waste processing system 100.

In general, the system 200 receives a food waste input 231, removes non-biodegradable waste 236 and outputs a biodegradable waste stream 234, for example, a biodegradable waste stream that can be processed and supplied to the digester 112. The system 200 includes a waste storage receptacle 216, an imaging system 235, a separation mechanism 236, a light source 238, a processing system 240 and a transport system 242.

The system 200 can include the imaging system 235 including one camera or a plurality of cameras depending on the embodiment. The imaging system 235 can be used in combination with light capturing equipment such as light and optic sensors. The imaging system 235 can capture either still images, video images or both still-image streams and video streams depending on the embodiment. The cameras can provide conventional images or video or HD images or video depending on the embodiment. In various embodiments, the cameras are configured to decrease the stream delay and optimize performance. Where multiple cameras are used, they can be located to provide images at different locations in the separation process. For example, a first camera can capture images of the food waste input 231 and one or more additional cameras can capture images at one or more separation stages included in the separation mechanism 236. One or more cameras can also be used in combination with the preceding to capture images of the biodegradable waste stream 234 after sorting as a quality control check.

The light source 238 can include any source of illumination suitable to light the subject of the imaging system 235. Accordingly, the light source 238 can include a single light or a plurality of lights as needed to illuminate the waste stream 231, 234 and waste separation 232. According to some embodiments, the light source 238 includes LED lighting. According to various embodiments, a color temperature of the light source 238 is selected to better illuminate a selected type of non-biodegradable material, for example, the non-biodegradable material that is most likely to be found in the food waste input 231 and/or non-biodegradable material that can disrupt the operation of the digester 112.

The processing system 240 can be provided as a standalone element in the waste processing system 100 or included in a centralized process control system, for example, the process control system 103. In various embodiments, the processing system 240 can be implemented in software, hardware or firmware or any combination thereof. Accordingly, any of the embodiments described herein can provide the image processing algorithms included in the system 200 in the form of a non-transitory computer readable medium in which instructions are stored that when executed by a processing system implement the image processing described herein. Depending on the embodiment, the processing system 240 can be executed by a central processing unit and/or a more specialized processor such as a graphics processing unit (GPU). Further, aspects of the image processing system 240 can be implemented with a specially-programmed, special purpose hardware, for example, an application-specific integrated circuit (ASIC). According to the illustrated embodiment, the processing system 240 includes a single-board microprocessor based minicomputer such as a RASPBERRY PI brand minicomputer with Wi-Fi wireless communication capabilities. In various embodiments, the imaging system 235 and the light source 238 are connected to the processing system 240.

In various embodiments, the processing system 240 includes memory storing a machine learning program employed for image processing. According to further embodiments, when executed by the processing system 240, the program operates to process the images captured by the imaging system 235 using a convolutional neural network. The image processing algorithm categorizes images based on a previously executed training data set to identify the non-biodegradable waste items included in the food waste input 231.

In various embodiments, the separation mechanism 236 can include one or a plurality of separation mechanisms. For example, any one of or a combination of magnets, electromagnets, and eddy current separators can be included to separate metals from the biodegradable waste stream. Other mechanisms that can be used alone or in combination with the preceding include by direct extraction using an automated robotic system, batch removal, sifting, or a similar separation mechanism. These mechanisms can be employed to remove foreign objects such as plastic, glass, and other materials from the biodegradable waste stream.

In some embodiments, a robotic arm is employed to scout through food waste to decrease the likelihood that non-biodegradable material remains undetected. For example, the robotic arm, a sifter, or any moving component can reshuffle the food waste to expose waste located at the bottom of the food waste input 231.

According to the illustrated embodiment, the waste storage receptacle 216 receives the non-biodegradable waste that is separated from the food waste input 231. Because different types of non-biodegradable waste can be selectively removed by the separating mechanism 236, the waste storage receptacle 216 can include a plurality of waste storage receptacles. For example, the waste storage receptacle 216 can include separate receptacles for ferrous metal, plastic, and non-ferrous metals, respectively. This approach can facilitate recycling efforts by separating the different materials for recycling. Further, in some embodiments, the waste storage receptacle 216 is located outside of the housing 130. Here, the non-biodegradable waste is transported by a chute or other means of conveyance from the separating mechanism 236 located in the housing 130 to the waste storage receptacle where the non-biodegradable waste can be picked up by a third party for recycling without any need to enter the housing 130 where the waste processing system 100 is located.

The transport system 242 moves the biodegradable waste from the separation mechanism 236 to the grinder, for example, the grinder 108 illustrated and described with reference to FIG. 1. Depending on the embodiment, the transport system 242 operates using a gravity feed system, an electromechanical system or a combination of the preceding. According to the illustrated embodiment, the transport system includes a motor driven conveyor system.

System response to detection of non-biodegradable material can be provided in a number of forms in combination with separating the non-biodegradable material from the waste stream. For example, depending on the embodiment, local alarming or other indications can be triggered, text messages or other alerts can be generated.

Figure 3:
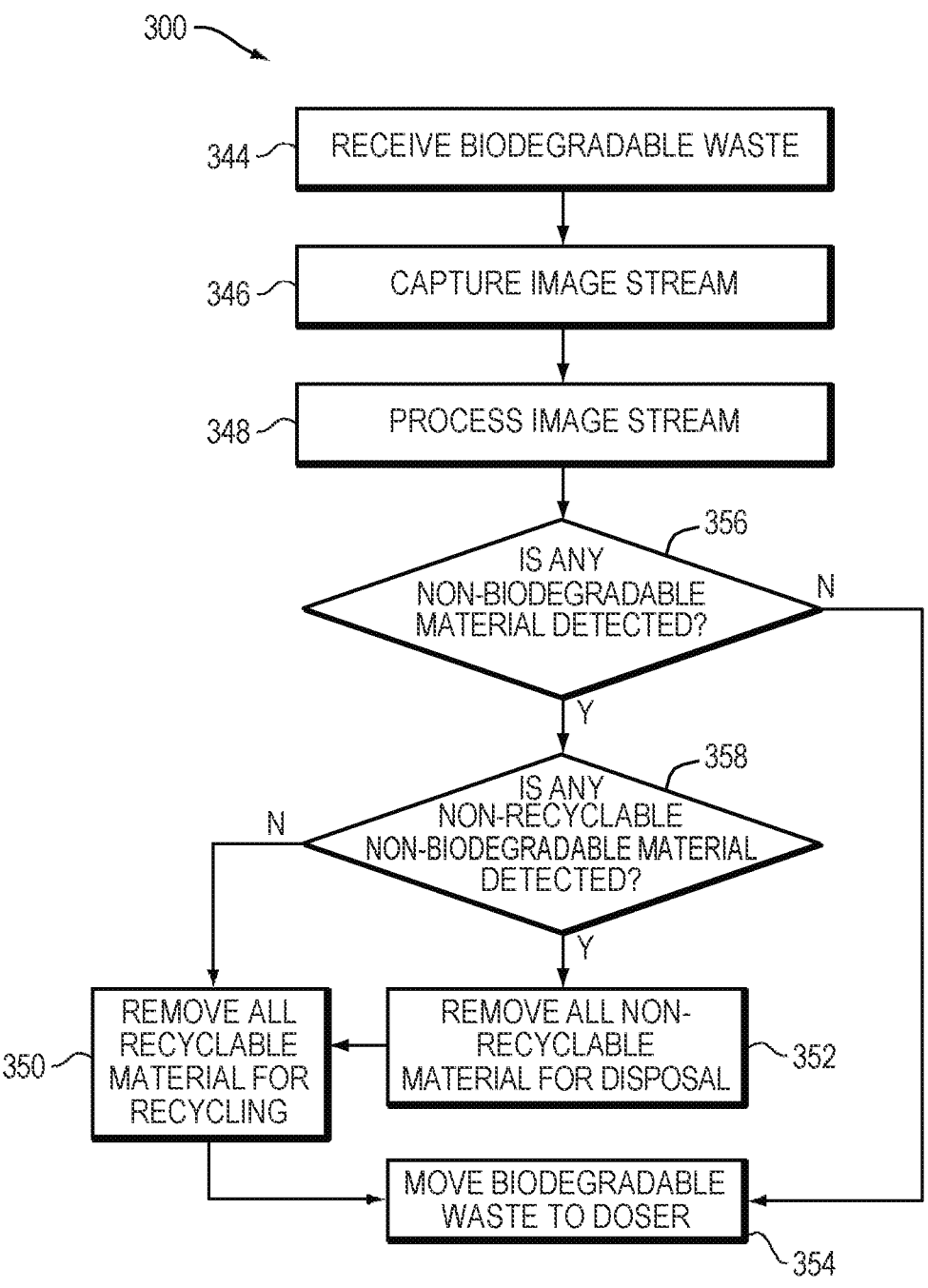
FIG. 3 illustrates a flow diagram of a process for separating waste in accordance with one embodiment.

Referring now to FIG. 3, a flow diagram of a process 300 employed in the waste processing system 100 is illustrated in accordance with one embodiment. According to some embodiments, the process 300 operates with the waste processing system 100 of FIG. 1 to evaluate the image stream captured by the imaging system 235. In these embodiments, the system operates to process the image streams to evaluate whether the food waste input 231 includes any non-biodegradable material, any non-recyclable material and remove the material before the waste is transported to the digester of the waste processing system 100.

In various embodiments, the process 300 includes actions and decision points. According to the illustrated embodiments, the actions include an act of receiving biodegradable waste 344, an act of capturing an image stream 346, an act of processing the image stream 348, an act of removing recyclable material 350, an act of removing non-recyclable material 352 and an act of moving the biodegradable waste to the doser 354. According to the illustrated embodiment, the decision points included in the process 300 include an act of determining whether any non-biodegradable material is detected in the waste stream 356, and an act of determining whether any non-recyclable, non-biodegradable material is detected in the waste stream 358.

According to the illustrated embodiment, the process 300 starts at the act of receiving biodegradable waste 344. The modular waste processing systems described herein can be conveniently located near the source of food waste. For example, the system can be placed in the vicinity of high-density residential buildings such as apartments and condos. Here, the biodegradable waste can be delivered to the waste processing system 100 by local residents. Systems can also be located at or near commercial establishments such as restaurants, food banks, and grocery stores that regularly dispose of volumes of food waste. According to these embodiments, biodegradable waste is sourced from nearby homes, businesses, and non-profit entities. This biodegradable waste can include food waste such as fruits, vegetables, waste oils, meat, dairy, grains, and beverages .In each instance, users can place the food waste directly into the waste receiving receptacle 102, for example, a food waste receptacle accessible from outside of the housing 130 in which the sorting, grinding and digesting processes take place.

At the act of capturing the image stream 346, an imaging system captures a stream of images of the food waste input. The image stream is communicated to the processing system 240. At the act of processing the image stream 348, the processing system 240 can include one or more algorithms that evaluate a series of images provided by one or more video streams to determine: a) whether the food waste input includes any material unsuitable for the anaerobic digestion process; and b) whether the unsuitable waste can be recycled. According to some embodiments, the image processing performed at the act 348 employs a convolutional neural network to categorizes materials and group them into acceptable and non-acceptable items within the waste stream, for example, where biodegradable waste is acceptable and non-biodegradable waste is unacceptable.

The process 300 continues at the act of determining whether any non-biodegradable material is detected in the waste stream 356. Here, the processing system 240 operates to determine whether any of the objects in the images includes non-biodegradable material that should not be further processed and delivered to the digester 112. If non-biodegradable material is not detected, the process moves to the act of moving the biodegradable waste to the doser 354, for example, as shown and described with reference to FIGS. 1 and 2. If non-recyclable material is identified at act 356, the process 300 moves to the act of determining whether any non-recyclable, non-biodegradable material is detected in the waste stream 358.

The waste processing system 100 including the foreign object detection and separation system 200 supports recycling in addition to the conversion of food waste into useful byproducts. At the act of determining whether any non-recyclable, non-biodegradable material is detected in the waste stream 358, the processing system 240 operates to determine whether any of the non-biodegradable objects or material in the images also includes non-recyclable material that should not be further processed and delivered to the digester 112. Where the system determines that all of the non-biodegradable material is recyclable (that is, there is no non-recyclable material among the non-biodegradable material) the process moves to the act of removing the recyclable material for recycling 350. According to various embodiments, the sorter 104 operates to separate the recyclable material into a separate waste stream to direct the recyclable material into a storage bin. The process then moves the act of moving the biodegradable waste to the doser 110.

Where non-recyclable material is identified at the act of determining whether any non-recyclable, non-biodegradable material is detected in the waste stream 358, the process moves to the act of removing the non-recyclable material for disposal 352. According to various embodiments, the sorter 104 operates to separate the non-recyclable material into a separate waste stream to direct the non-recyclable material into a different storage bin than the recyclable material. According to the illustrated embodiment, the process 300 then moves the act of removing the recyclable non-biodegradable waste for recycling 350. Following the acts, 352 and 350 the remaining waste in the waste stream only includes food waste. The process then moves the act of moving the biodegradable waste to the doser 110.

Figures 4, 5:
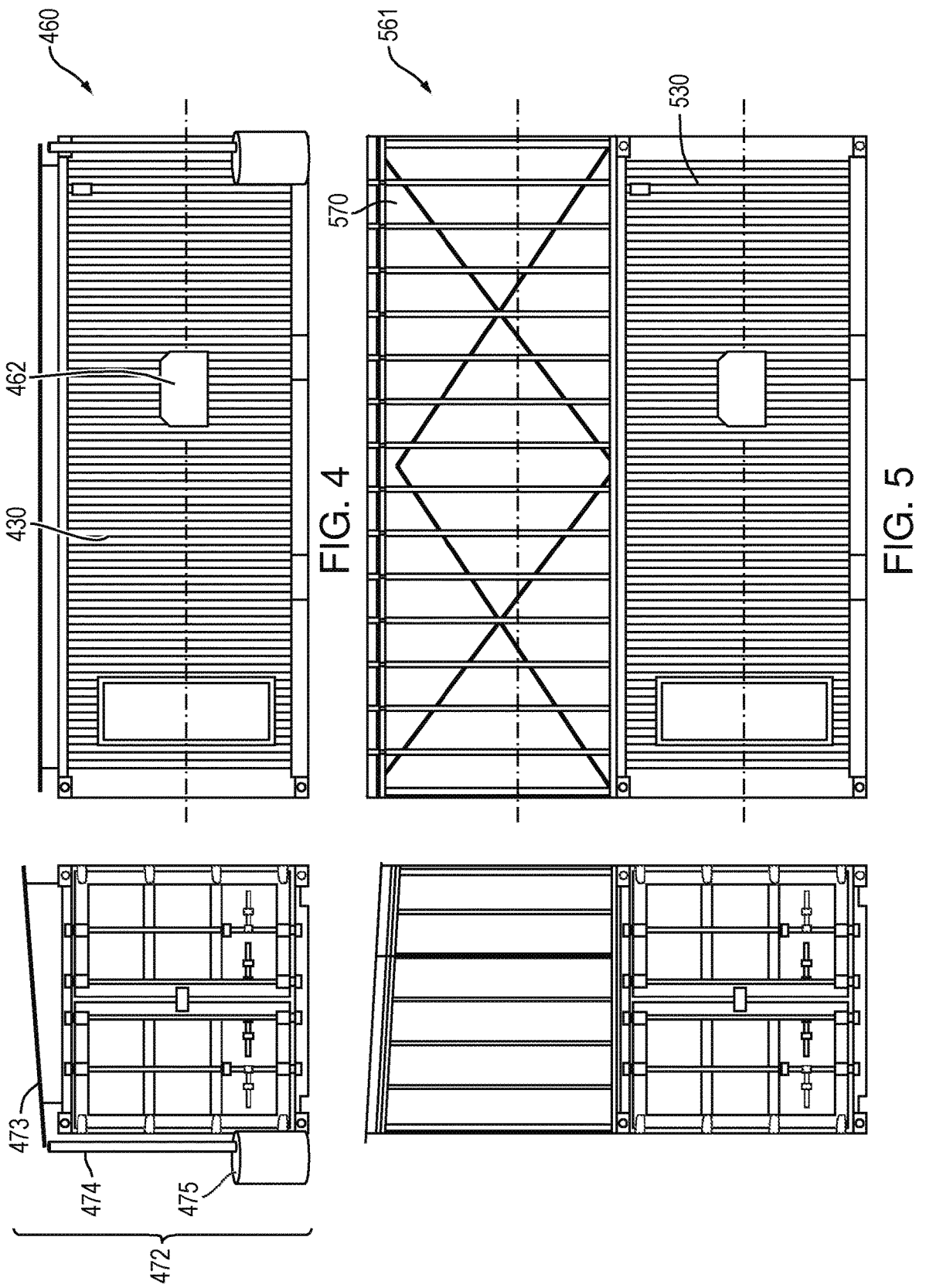
FIG. 4 illustrates a plan view of a waste processing system in accordance with one embodiment.
FIG. 5 illustrates a plan view of a waste processing system in accordance with another embodiment.

Referring now to FIG. 4, a plan view of a waste processing system 460 is illustrated in accordance with one embodiment. The waste processing system 460 includes a housing 430, a waste receiving port 462 and a water recovery system 472. A slanted roof 473, a downspout 474 and a rain barrel 475 included in the water recovery system 472 are also illustrated in FIG. 4.

The housing 430 provides an enclosure for the components of the waste processing system, for example, the waste processing system 100 as illustrated and described with reference to FIG. 1. According to one embodiment, the housing is provided by a repurposed shipping container, for example, an 8 ft. by 8 ft. by 20 ft. long shipping container. According to another embodiment, an 8 ft. by 8 ft. by 10 ft shipping container is used to provide a more compact system with a smaller footprint on site. All of the preceding provides a modular form factor that can be shipped to a site that is a local source of food waste.

According to various embodiments, the housing 430 provides a secure enclosure for a food waste processing system including an anaerobic digester to prevent access within the enclosure by untrained and unauthorized personnel. However, the housing 430 also allows personnel untrained in an operation of the food waste processing system to safely deposit food waste from a location outside of the enclosure for automatic processing by the system. Further, these embodiments also allow personnel untrained in the operation of the food waste processing system to access a liquid fertilizer dispensing tap where the tap is accessed from outside of the enclosure. This arrangement of processing equipment is particularly advantageous for siting mobile food waste processing systems at a point-of-source of food waste delivered by hand in small batches by members of the local community.

The system 460 can be configured to provide a robust standalone food waste processing hub suited for a substantially automated operation. According to these embodiments, the system 460 provides a convenient and safe facility for the receipt and anaerobic processing of food waste. These modular systems can allow personnel untrained in the operation of the anaerobic digester system safely place food waste at an input to the anaerobic digestion system.

The housing 430 provides a weather-proof and insulated enclosure to house the waste processing system 100. According to various embodiments, the insulation of the outer walls of the housing 130 (including the ceiling) are insulated to provide a minimum insulation rating of R-19. According to one embodiment, the insulation is a minimum of six inches thick. Applicant has found that this level of insulation can provide the system 460 with an energy efficient construction suitable for a self-contained, autonomous system 460 that can operate independent of the local electrical grid and any outside sources of water. The preceding can be supported by modifications concerning individual components of the waste processing system 100. For example, the digestion tank can be separately insulated to provide a minimum insulation rating of R-13. According to one embodiment, the digestion tank is insulated with a minimum of four-six inches of insulation. The level of insulation of other components included in the waste processing system 100 can also be increased. These modifications reduce the burden on any heating system or water heating system included in the system. For example, a reduction in the required BTU output of these heating systems reduces the consumption of biogas and/or electrical energy that is used to heat the housing 430 and/or process-water.

According to the illustrated embodiment, the water recovery system 472 is installed to collect rainwater. Here, the slanted roof 473 and gutter system (not shown) direct rain water to the downspout 474. The captured rainwater runs down the down spout 474 where it is collected in the rain barrel 475. The water recovery system can also include a sieve and/or a filter to remove particulate and other contaminants from the collected water when it is pumped into the waste processing system 100. According to one embodiment, the collected and purified water is pumped to a holding tank included in the water source 118, referring to the waste processing system 100. According to other embodiments, the water recovery system 472 can include an integral air moisture capture system for use in regions with high humidity or a micro-desalination system for use in arid regions.

The system 460 can also include various forms of electricity generating equipment. In accordance with one embodiment, a biogas fueled electrical generator is included in the system 460. In another embodiment, solar panels can be included in the system 460 to provide electricity. In either approach, a battery system can also be included to store electrical energy for future use by the waste processing system 100. According to these embodiment, the use of a biogas fueled generator and/or integral solar panels supports the self-contained, autonomous operation of the system 460.

According to the illustrated embodiment, the waste receiving port 462 is accessible at an exterior of the housing 430 to couple to a waste receiving receptacle and associated hardware included within the housing 430. As described above with reference to the waste receiving receptacle 102 of FIG. 1, the waste receiving receptacle and associated hardware can include any of a chute, a latching lid, a drawer, a rolling drawer, a tube, a window, a ramp, a drop box, a conveyor belt, a bin or a bucket. According to one embodiment, the waste receiving port 462 includes a spring loaded, hinged outer door that is pulled open by the user to provide access to a chute. The chute provides a gravity feed for the food waste from the outer door to the sorter included in the system 460.

Referring now to FIG. 5, a plan view of a waste processing system 561 is illustrated in accordance with one embodiment. The waste processing system 561 includes a housing 530 with an integral greenhouse 570 located above and secured to the roof of the housing 530. Here too, the housing 530 provides an enclosure for the components of the waste processing system, for example, the waste processing system 100 as illustrated and described with reference to FIG. 1. Access to the greenhouse 570 can be provided via a set of stairs or a ladder from within the housing 530.

According to these embodiments, the greenhouse 570 provides an integral agricultural system where a portion of the liquid fertilizer that is output by the waste processing system 100 can be used to fertilize the crops being grown in the greenhouse 570. Additionally, any water wasted from the greenhouse can be used as a water source to add to the water source 118. The overall sustainability and efficiency of the system is further improved where the biogas and/or excess heat produced by the system is employed to heat the greenhouse 570 in cold weather. A variety of different crops can be grown in the greenhouse. According to some embodiments, micro-greens are grown in the greenhouse 570. According to further embodiments, a hydroponic growing operation is housed in the greenhouse 570. These embodiments employ natural light for photosynthesis and the biogas byproduct and/or heat of anaerobic digestion is used to heat the greenhouse 570 and the water employed by the hydroponic system.

While not illustrated, the waste processing system 561 can include any of the water recovery systems illustrated and/or described with reference to the system 460. For example, a partial or otherwise modified version of the slanted roof 473 and associated water recovery system elements can be included so long as they do not negatively impact operation of the greenhouse.

Figure 6:
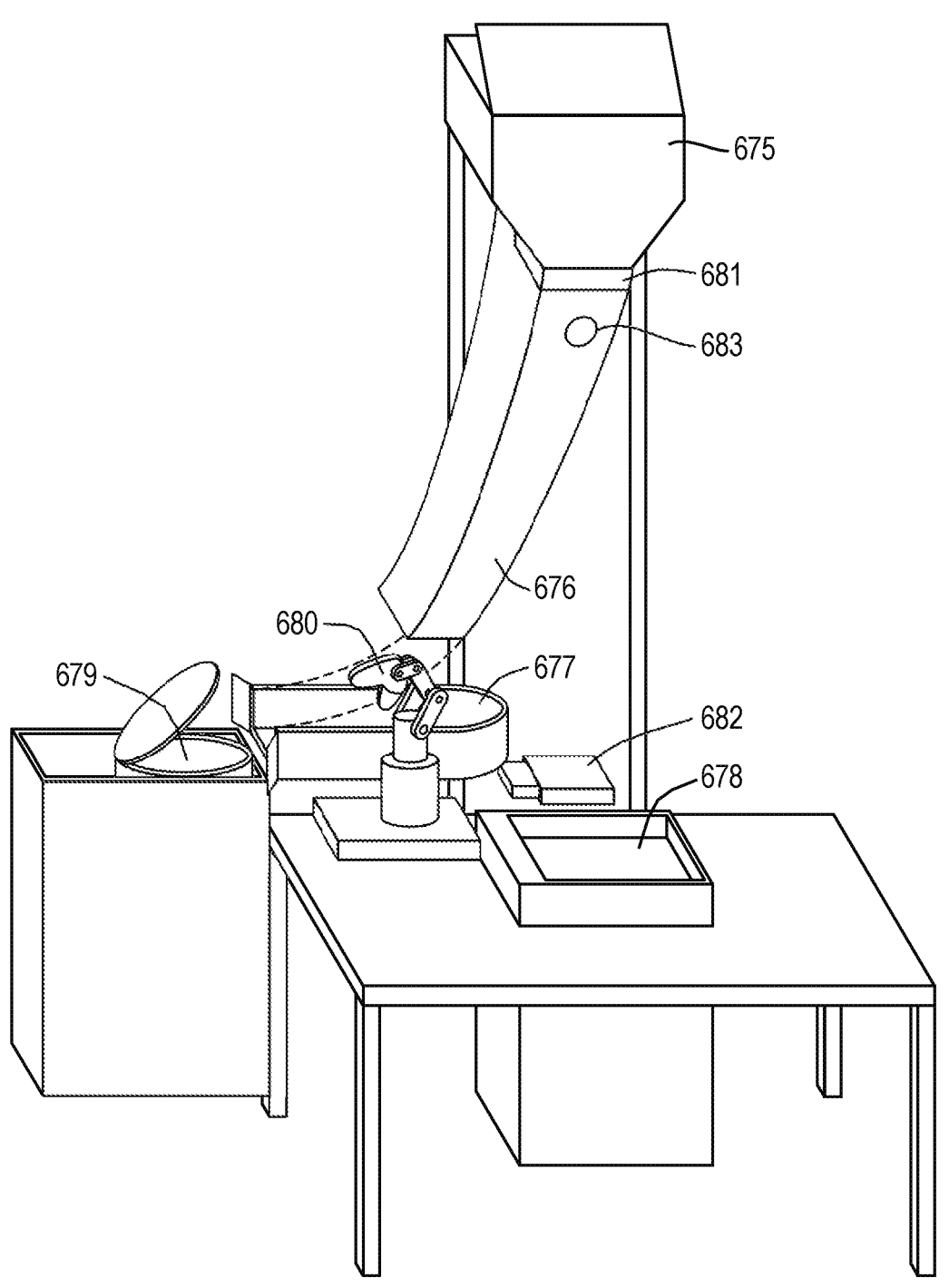
FIG. 6 illustrates an isometric view of a waste sorting system in accordance with one embodiment.

FIG. 6 illustrates an isometric view of a waste sorting system 600 in accordance with some embodiments. The waste sorting system 600 includes an input receptacle 675, a chute 676, a sorting receptacle 677, a first waste receptacle 678, a second waste receptacle 679 and a robotic arm 680. The waste sorting system 600 also includes a first actuator 681, a second actuator 682 and a water inlet 683. According to various embodiments, the waste sorting system 600 includes one or more elements described with reference to the waste receiving receptacle 102, sorter 104 and non-biodegradable waste storage 116 of FIG. 1. The general operation of the waste sorting system 600 includes receipt of food waste input to the waste processing system 100, and the separation and removal of non-biodegradable material from the food waste input stream to create a biodegradable input stream.

The input receptacle 675 is located adjacent a point at which food waste is first received such as the waste receiving port 462 illustrated and described with reference to FIG. 4 and the waste processing system 460. According to the illustrated embodiment, the input receptacle 675 includes a drop box that can be provided in the form of a bin or a bucket. The input receptacle 675 includes a lid, for example, a partial covering that acts as a splash guard for the input receptacle 675. The input receptacle 675 also includes an outlet from which a controlled discharge of the food waste input stream can be released from the input receptacle 675 for sorting. According to the illustrated embodiment, the outlet includes a moveable panel or other mechanical structure that blocks the outlet when in a closed position but allows the discharge of food waste from the input receptacle 675 when in an open position. In the illustrated embodiment, the first actuator 681 operates to move the panel in a controlled manner between the closed position and the open position. According to some embodiments, the first actuator is a linear actuator that provides a precise degree of control of the amount to which the mechanical structure that shuts the outlet is open. This level of control along with a control of an amount of time that the first actuator 681 maintains the discharge in an open state provides a more precise controlled release of food waste from the input receptacle 675. For example, the amount of food waste being processed can be controlled to manage operation of the waste processing system based on a current capacity of the various pieces of process equipment (such as the sorter 104, grinder 108, doser 110 and digester 112 illustrated in FIG. 1).

According to the illustrated embodiment, the input receptacle 675 is coupled to the chute 676 at the outlet where it provides a gravity feed for the food waste discharged from the input receptacle 675 to the sorting receptacle 677. The chute 676 also includes a water inlet 683. The water inlet 683 is provided as a source of water to add to the food waste input stream to improve the moisture content for processing by the waste processing system 100 or by the system 700 described below with reference to FIG. 7.

In the illustrated embodiment, the chute 676 directs the food waste discharged from the input receptacle 675 directly to the sorting receptacle 677. In various embodiments, an imaging system, for example, a video camera, is directed at the sorting receptacle 677. As described in greater detail elsewhere herein, images of food waste located in the sorting receptacle 677 are processed by an image processing system including a convolutional neural network. According to some embodiments, the image processing system operates in substantially real time to identify non-biodegradable material located in the sorting receptacle 677. The term "substantially" as used herein with reference to real time image processing, refers to image processing that occurs fast enough that a human observer is unaware of any latency between receipt of a current image(s) and an initiation of a sorting operation by the robotic arm to remove non-biodegradable material identified in the image(s). In one embodiment, the non-biodegradable material that can be identified for removal includes both of plastic material and metals. According to a further embodiment, the plastic material includes microplastics. The image processing system operates to communicate the identification and location coordinates of the non-biodegradable material to the sorting mechanism(s) for example, the robotic arm 680.

According to various embodiments, the sorting operation includes an iterative process by which the robotic arm 680 operates to move the food waste around within the sorting receptacle 677 in a deliberate and controlled manner to allow the imaging system to capture images of more of the food waste. For example, the depth of the distal end of the robotic arm 680 can be controlled to selectively scrape an upper layer of a mass of food waste at various depths where the imaging system can capture improved images of the lower layers of the food waste in the receptacle 677. Other operations of the robotic arm can assist in various embodiments. These include picking up and relocating food waste within the sorting receptacle 677, turning food waste over in the receptacle and restacking food waste within the receptacle and moving the food waste to another location in the receptacle. In some embodiments, the sorting process is a timed process that occurs for a set period of time before the sorting receptacle is emptied 677 for a receipt of a new batch of food waste.

In one embodiment, the image processing system includes a non-transitory computer readable storage medium to store instructions, a processor coupled to the non-transitory computer readable medium to process the stored instructions to: receive at least one image of the food waste deposited in the sorting receptacle 677; automatically perform processing on the image using a convolutional neural network to identify the non-biodegradable material in the sorting receptacle, which can include both plastic and metal material; generate instructions by which the robotic arm 680 automatically selects and removes one or more pieces of non-biodegradable material that are identified by the image processing system, the instructions transforming information concerning pixel coordinate locations of the non-biodegradable material in the image(s) to locations of the non-biodegradable material in the sorting receptacle. According to other embodiments, an automated sorting systems can include other technology including magnets, sifters and shredders employed alone or in combination with one or more of the preceding and the robotic arm.

In various embodiments, the robotic arm 680 is an articulating arm that can move thru multiple axes to screen, sort and remove the non-biodegradable material and place it in the first waste receptacle 678. In some embodiments, the robotic arm 680 operates to move the food waste within the sorting receptacle 677 to provide the imaging system with different views of the food waste. This approach generates a larger set of images including a wider variety of views of the same set of food waste to the image processing system to increase the percentage of the non-degradable biodegradable material that is identified and removed.

According to the illustrated embodiment, the first waste receptacle 678 receives the non-biodegradable waste that is separated from the food waste. That is, the robotic arm 680 operates to grasp the non-biodegradable material as identified by the image processing system, lift it out of the sorting receptacle 677 and place it in the first waste receptacle 678.

According to the illustrated embodiment, the sorting receptacle 677 includes an open end, at least one moveable panel, side walls and a closed end. The second actuator is coupled to the closed end of the sorting receptacle 677. According to one embodiment, the sorting receptacle 677 includes a tilt tray that is operated by the second actuator 682. According to this embodiment, the contents of the sorting receptacle 677 are emptied with assistance of the second actuator 682. That is, the second actuator 682 operates to articulate the sorting receptacle 677, for example, by raising the closed end such that the food waste is discharged out of the open end of the receptacle. According to some embodiments, the second actuator 682 tilts the sorting receptacle 677 at an angle of at least 45 degrees relative to horizontal. According to some embodiments, the second actuator 682 is a linear actuator. According to further embodiments, the sorting receptacle 677 includes a scale that provides feedback concerning a mass of the material in the sorting receptacle 677. In these embodiments, the sorting receptacle 677 is emptied when a desired amount of material (measured by weight) is present in the receptacle 677 when sorting is complete.

The second waste receptacle 679 provides a storage area for the biodegradable food waste stream that is discharged from the sorting receptacle 677. According to some embodiments, the sorting receptacle includes a sink. In various embodiments, the contents of the sorting receptacle 677 are received by the second waste receptacle 679 for further processing to prepare the biodegradable food waste input stream for an anaerobic digester. In some embodiments, the waste sorting system 600 can be included in either the waste processing system 100 illustrated and described with reference to FIG. 1 or the system 700 illustrated and described immediately below with reference to FIG. 7.

Figure 7:
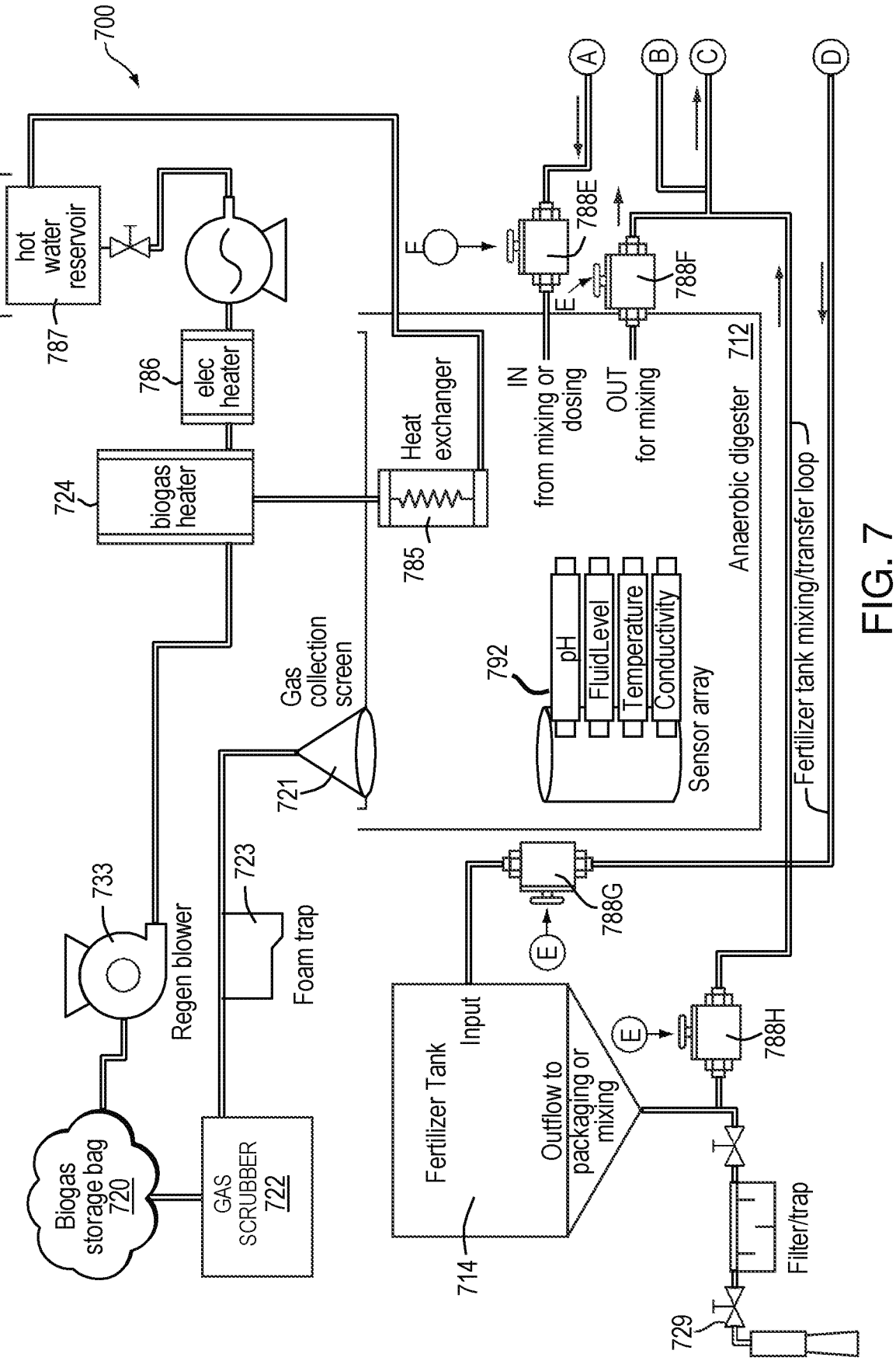
FIG. 7 illustrates a schematic diagram of a waste processing system in accordance with one embodiment.
Figure 7:
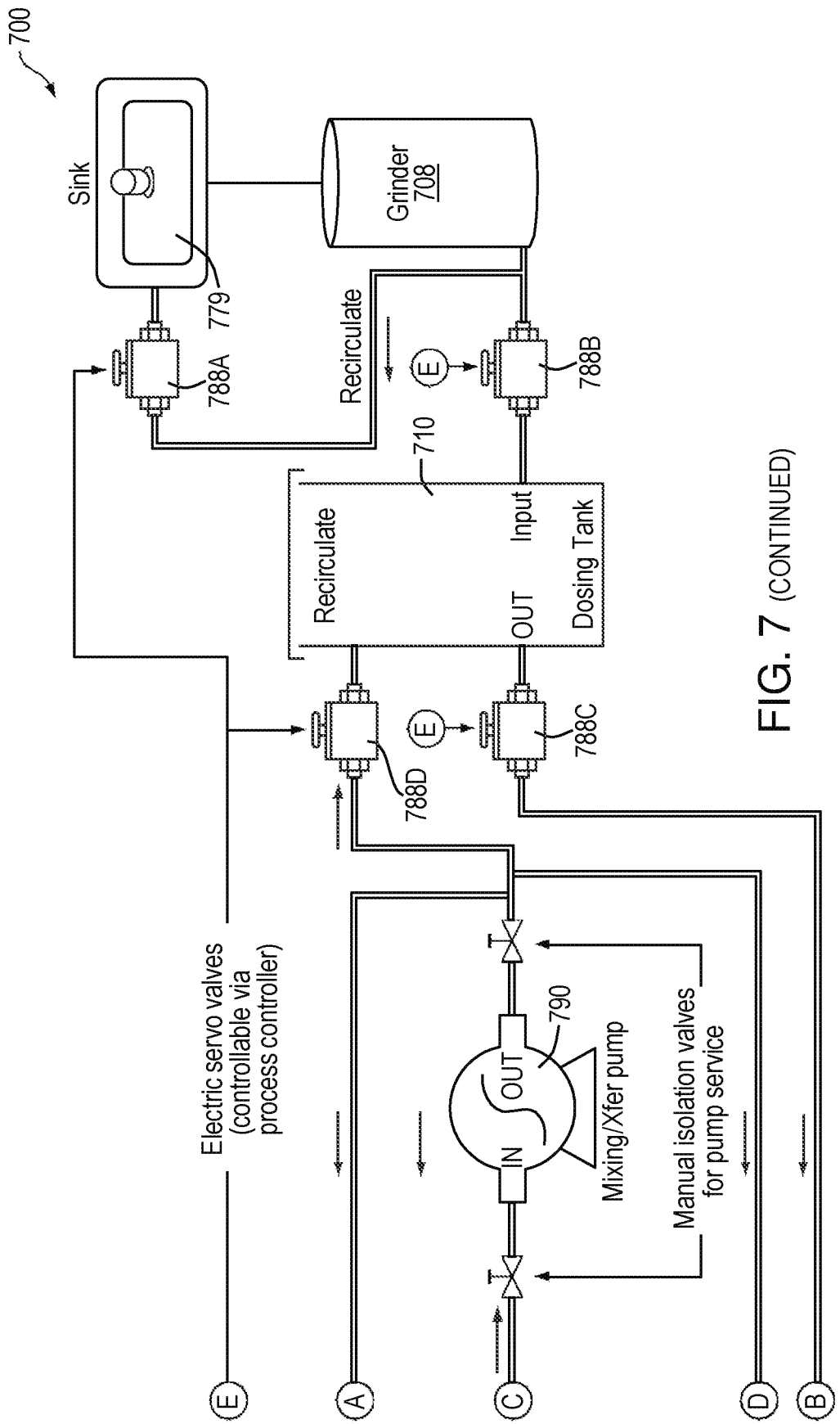

Referring now to FIG. 7, a system 700 for food waste processing is illustrated in accordance with various embodiments. According to some embodiments, the system 700 is included in an automated system that processes a food waste input and generates a liquid fertilizer output. For example, the system 700 can be included in a complete food waste processing system that also includes the food waste sorting systems as illustrated and described elsewhere herein. In further embodiments, the system 700 is provided in a self-contained secure housing that prevents access to process components but allows personnel untrained in the operation of the system 700 to safely access both a food waste input to the system and a system output from which a liquid fertilizer is dispensed from the system 700. In some embodiments, the housing including the system 700 and waste sorting system 600 is delivered to a site where it is connected to an external electrical supply and an external source of water. According to other embodiments, the system 700 (including fully automated embodiments) is entirely self-contained including an integral water storage tank and electrical generation as described above.

According to the illustrated embodiment, the system 700 includes a grinder 708, a dosing tank 710, an anaerobic digester 712, a fertilizer tank 714, a biogas storage bag 720, a gas scrubber 722 and a biogas heater 724. The biogas system also includes a gas collection screen 721, a foam trap 723, and a regenerative blower 733. The water heating system also includes a heat exchanger 785, an electrical water heater 786, a hot water reservoir 787 and a water pump 789. The system 700 also includes a waste receptacle 779 and a centralized fluid control system. The centralized fluid control system includes a plurality of electrically operated servo valves 788A-788H and a main pump 790. In various embodiments, control of the system 700 (including the centralized fluid control system) is provided by a process control system, for example, the process control system 103 illustrated in FIG. 1.

The waste receptacle 779 receives food waste after sorting is completed to remove non-biodegradable waste included in the food waste that is input to the system 700. For example, the waste receptacle 779 can be included as the second waste receptacle 679 in the sorting system 600 as illustrated and described with reference to FIG. 6. Further, the sorting system 600 illustrated and described with reference to FIG. 6 is included in the system 700 in various embodiments. The waste receptacle 779 provides a location for the addition of water to the biodegradable food waste input stream that is supplied from the sorting system 600. For example, water supplied at the water inlet 683 included in the sorting system 700 can be captured in the waste receptacle 779 along with the biodegradable input stream. In the illustrated embodiment, the waste receptacle 779 includes an outlet where the biodegradable food waste input stream is discharged to the grinder 708. In one embodiment, the biodegradable food waste input stream travels from the waste receptacle 779 to the grinder 708 via the force of gravity. The waste receptacle is also coupled to the grinder 708 via a first recirculation loop. According to some embodiments, the integral pump included in the grinder is employed to move fluid through the recirculation loop to assist in discharging newly received biodegradable food waste from the waste receptacle 779.

The grinder 708 operates to grind and macerate the biodegradable food waste input stream received from the sorting system 600 via the waste receptacle 779. According to some embodiments, the grinder 708 also includes an integral fluid pump capable of discharging the biodegradable food waste input stream processed by the grinder 708 out the discharge outlet for the grinder. According to the illustrated embodiment, the discharge outlet is coupled to process piping that includes a primary fluid path coupled to a second electrically operated servo valve 788B. The discharge outlet is also coupled to process piping that includes the first recirculation loop that connects the output of the grinder 708 to the waste receptacle 779 via a first electrically operated servo valve 788A. The primary fluid path connects the grinder 708 to the dosing tank 710.

The dosing tank 710 provides a relatively large capacity storage tank for storing the biodegradable food waste input stream processed by the grinder 708 before the processed food waste is moved to the anaerobic digester 712. According to the illustrated embodiment, the dosing tank 710 does not include a pump. In the illustrated embodiment, the dosing tank 710 includes the input coupled to the grinder 708, an output coupled to an inlet of the main pump 790 via a third electrically operated servo valve 788C and a recirculation input coupled to an outlet of the main pump 790 via a fourth electrically operated servo valve 788D.

In various embodiments, the anaerobic digester 712 operates to break down food waste in the absence of oxygen. For example, the anaerobic digester 712 can include a sealed vessel (a "reactor") that receives the biodegradable food waste input in the form of food waste slurry output from the dosing tank 710 and generates outputs including biogas and a digestate in the form of liquid fertilizer that is discharged to the fertilizer tank 714. In the illustrated embodiment, the anaerobic digester 712 includes an input coupled to the outlet of the main pump 790 via a fifth electrically operated servo valve 788E and an output coupled to an inlet of the main pump 790 via a sixth electrically operated servo valve 788F. Various sensors can be included for real-time monitoring of parameters concerning the state of the anaerobic digestion process as indicated by the current state of the fluid being processed within the digester 712. In the illustrated embodiment, the anaerobic digester 712 includes a sensor array 792 that includes a pH sensor, a fluid level sensor, a temperature sensor and a conductivity sensor. Feedback provided by the sensor array to the process control system allows the anaerobic digestion process to be controlled for efficient anaerobic digestion process and the methane yield. This includes maintaining proper pH levels, adequate conductivity, a proper temperature range and fluid level in the digester 712.

The fertilizer tank 714 operates to store the liquid fertilizer effluent received from the anaerobic digester 712 before it is dispensed as fertilizer. According to the illustrated embodiment, the fertilizer tank 714 includes a cylindrical, cone-shaped tank that helps prevent sedimentation and clogging of liquid fertilizer lines. In the illustrated embodiment, the fertilizer tank 714 includes an input coupled to the outlet of the main pump 790 via a seventh electrically operated servo valve 788G and an output that is coupled to both an inlet of the main pump 790 via a eighth electrically operated servo valve 788F and to a fertilizer dispensing valve 729.

In some embodiments, the fertilizer dispensing valve 729 is accessible outside of a self-contained secure housing in which the remainder of the system 700 is located. The fertilizer dispensing valve 729 allows for the withdrawal of liquid fertilizer that is generated from the biodegradable food waste input stream supplied as an output of the sorting system illustrated in FIG. 6. According to some embodiments, a faucet is located at the outlet side of the fertilizer dispensing valve 729. The fertilizer dispensing valve 729 can include an automated valve whose operation is controlled by the process control system that controls an overall operation of the system 700. For example, the fertilizer dispensing valve 729 can be controlled to dispense a predetermined amount of liquid fertilizer to fill a container having a known volume. In some embodiments, an end user can employ a mobile app on their own electronic device (for example, phone or tablet) in combination with the waste processing system 700 to control an operation of the fertilizer dispensing valve 729 to dispense liquid fertilizer in known amounts.

The gas collection screen 721 is positioned above the fluid in the anaerobic digester 712 to collect biogas generated by the anaerobic digestion process. In one embodiment, the gas collection screen is in the form of an inverted drum that extends down into the fluid in the digester to provide a seal. According to this embodiment, an elevation of the gas collection screen can be adjusted to accommodate changes in the fluid level in the anaerobic digester 712. The biogas that is collected is a methane rich byproduct that is further processed for use within the system 700. According to the illustrated embodiment, the foam trap 723 operates to eliminate foam that can build-up on the surface of liquid in the anaerobic digester 712. Operation of the foam trap assists in preventing the ingress of foam into the process piping of the gas system. The gas scrubber 722 is employed to remove hydrogen sulfide and water vapor from the biogas to provide a purer form of methane gas for use within the system 700.

The biogas storage bag 720 provides a storage volume for biogas that allows the system 700 to control the gas pressure in the gas system. In some embodiments, the biogas storage bag is manufactured of a flexible membrane material. This allows the volume of biogas stored in the biogas storage bag 720 to adjust while in use. According to the illustrated embodiment, the regenerative blower 733 is located on an output side of the biogas storage bag 720. In operation, the regenerative blower 733 moves the biogas through the gas system, for example, from the biogas storage bag 720 to the biogas heater 724.

A closed loop hot water heating system includes the biogas heater 724, the heat exchanger 785, the electrical water heater 786, the hot water reservoir 787 and the water pump 789. The heat exchanger 785 is located in the anaerobic digester 714. In operation, the heat exchanger 785 is submersed in the fluid found in the anaerobic digester 714. The hot water circulated through the heat exchanger 785 transfers heat to the fluid in the anaerobic digester 714 to control a temperature of the fluid. The biogas heater includes a gas input connected to the biogas storage bag 720 via the regenerative blower 733 and a water input from the heat exchanger closed loop system and a water output connected to an input of the heat exchanger 785. The biogas heater 724 is a gas operated hot water heater that is fueled by biogas. According to the illustrated embodiment, the electric water heater 786 provides another source of heat employed in the closed loop system. Here, an electrical heating element is employed to heat water circulated in the closed loop system. The hot water reservoir 787 can include an insulated tank to store water that is circulated in the closed loop system. A line supplying make-up water (not illustrated) can also be included in the system. The water pump 789 is employed to circulate the water in the hot water closed loop system.

The system 700 also includes a process control system (not illustrated, but for example as illustrated and described with reference to FIG. 1) to provide automated control of the processing of the biodegradable food waste input to the system. Applicant finds that the piping schematic including the locations and control of the electrically operated servo valves 788A-788H in the system 700 facilitate an automated operation of a modular, self-contained food waste processing system that was not previously possible. That is, a precise automated control provided by the system 700 allows operation and control while also permitting untrained personnel with limited safe access to allow food waste to be input to the system and liquid fertilizer to be withdrawn from the system while the system is operating unmanned.

For example, the movement of process fluid in the system between the dosing tank 710, the anaerobic digester 712 and the fertilizer tank 714 is accomplished using a single pump, the main pump 790 coupled to a pump-inlet header and a pump-outlet header that are each common to the dosing tank 710, the anaerobic digester 712 and the fertilizer tank 714. Through proper valve sequencing, the equipment layout and connections illustrated in FIG. 7 allow the single main pump 790 to efficiently deliver an automated process operation to control tank levels, process flows and the characteristics of the fluid found in any of the dosing tank 710, the anaerobic digester 712 and the fertilizer tank 714. Through proper feedback and control the different fluid conditions (the biodegradable food waste input includes a high percentage of solids while the fertilizer is dispensed as a liquid) found in different stages of the system 700 can be controlled to maintain the system 700 operating at a high efficiency to produce the liquid fertilizer and biogas.

For example, a first pair of electrically operated servo valves 788A, 788B are operated to control the tank level and fluid conditions found in the grinder 708. The biodegradable food waste input is loaded into the grinder 708 with each of the first pair of electrically operated servo valves 788A, 788B closed. Operation of the grinder 708 along with the addition of water as needed to produce an output slurry with the desired fluid characteristics can require periodic recirculation of the material in the grinder 708. The recirculation can also prevent a build-up of sediments in the grinder 708. For recirculation, the process control system (for example, process control system 103) opens the first valve 788A while maintaining the second valve 788B closed. The system operates a pump integral to the grinder 708 to recirculate the contents of the grinder 708 via a loop including the waste receptacle 779. The contents of the grinder 708 are discharged when the process control system operates to turn on the grinder-pump while maintaining the first valve 788A in a closed state and opening the second valve 788B.

Fluid recirculation and discharge for the dosing tank 710 are controlled similarly but with the main pump operating instead of the grinder-pump. Here, a second pair of electrically operated servo valves 788C, 788D are operated to control the tank level and fluid conditions found in the dosing tank 710. The fluid discharged from the grinder 708 is received by the dosing tank. For recirculation, the process control system opens the both the third valve 788C and the fourth valve 788D while turning the main pump 790 on. The control system also maintains the remaining electrically operated servo valves 788A, 788B, 788E, 788F, 788G, 788H in a closed state. This creates a recirculation loop from the output of the dosing tank to the inlet of the main pump 790 via the third electrically operated servo valve 788C. The fluid output from the dosing tank is discharged via the pump outlet to the recirculation input of the dosing tank 710 via the fourth electrically operated servo valve 788D.

The process control of the anaerobic digester 712 includes a similar overall approach. Here, the sensor array 792 included in the anaerobic digester provide the process control system feedback in the form measurements concerning the characteristics of the fluid found in the digester 712. The process control system can, for example, initiate recirculation or other operations to move fluid within the system 700 to maintain proper operating conditions in the anaerobic digester 712. A third pair of electrically operated servo valves 788E, 788F are operated to control the tank level and fluid conditions found in the anaerobic digester 712. The fluid discharged from the dosing tank 710 is received by the digester 712. This operation is performed with the process control system opening the third valve 788C to feed the inlet of the main pump 790, and the fifth valve 788E to connect the anaerobic digester 712 inlet to the outlet of the pump 790. The control system opens the two valves 788C, 788E while turning on the main pump 790 and maintaining the remaining electrically operated servo valves 788A, 788B, 788D, 788F, 788G, 788H in a closed state. A mixing operation for the anaerobic digester 712 occurs with the process control system opening the electrically operated servo valves 788E, 788F while turning the main pump 790 on. This creates a recirculation loop from the output of the anaerobic digester 712 to the inlet of the main pump 790 via the sixth electrically operated servo valve 788F where the fluid discharged from the pump is returned to the anaerobic digester via the fifth electrically operated servo valve 788E. The process control system maintains the remaining electrically operated servo valves 788A, 788B, 788C, 788D, 788G, 788H in a closed state during the mixing operation.

The fluid levels and characteristics in the fertilizer tank 714 are also precisely controlled in an automated manner in the system 700. A sixth pair of electrically operated servo valves 788G, 788H are operated to control the tank level and fluid conditions found in the fertilizer tank 714. The fluid discharged from the anaerobic digester 712 is received by the fertilizer tank 714. This operation is performed with the process control system opening the sixth valve 788F to feed the inlet of the main pump 790, and the seventh valve 788G to connect the fertilizer tank 714 input to the outlet of the pump 790. The control system opens the two valves 788F, 788G while turning on the main pump 790 and maintaining the remaining electrically operated servo valves 788A, 788B, 788C, 788D, 788E, 788H in a closed state. A mixing operation for the fertilizer tank 714 occurs with the process control system opening the electrically operated servo valves 788G, 788H while turning the main pump 790 on. This creates a recirculation loop from the output of the fertilizer tank to the inlet of the main pump 790 via the eighth electrically operated servo valve 788H where the fluid discharged from the pump is returned to the fertilizer tank 714 via the seventh electrically operated servo valve 788G. The process control system maintains the remaining electrically operated servo valves 788A, 788B, 788C, 788D, 788E, 788F in a closed state during the mixing operation.

While the food waste processing systems are illustrated and described with reference to an anaerobic digestion system, other digestion or incineration technologies can be employed to process the biodegradable waste. For example, aerobic digestion, animal feed, composting, gasification, fluidized bed, pyrolysis, thermal treatment, and other waste-to-energy technologies.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An automated food waste processing system, the system comprising:

an enclosure secured to prevent unauthorized access to contents contained therein, the enclosure including a plurality of exterior walls; and a food waste processing system housed within the enclosure, the food waste processing system including:
an anaerobic digester;
a sorting receptacle configured to receive a food waste input stream for the anaerobic digester, the food waste input stream including food waste and non-biodegradable material;
an imaging system configured to capture a plurality of images of the food waste and the non-biodegradable material received by the sorting receptacle;
a processing system configured to process the plurality of images using a trained neural network to identify at least plastic waste and metal waste as the non-biodegradable material when included in the food waste input stream as received by the sorting receptacle, the plastic waste and the metal waste identified for removal from the food waste input stream; and
a port coupled to the sorting receptacle, the port accessible at an outside surface of an exterior wall included in the plurality of exterior walls, the port configured to allow personnel untrained in an operation of the food waste processing system to deposit the food waste input stream from a location outside of the enclosure.

2. The automated food waste processing system of claim 1, further comprising:
an input receptacle having an outlet, the input receptacle coupled to the port and configured to receive the food waste input stream that is deposited at the port; and
an actuator configured to automatically release a set amount of material included in the food waste input stream from the input receptacle via the outlet for delivery to the sorting receptacle.

3. The automated food waste processing system of claim 2, further comprising a chute coupled to the outlet, the chute configured to automatically direct the set amount of material released from the input receptacle to the sorting receptacle.

4. The automated food waste processing system of claim 3, further comprising:
a sorting system including a robotic arm configured to automatically locate and remove the non-biodegradable material from the sorting receptacle and deposit the non-biodegradable material for disposal, the automated operation of the robotic arm guided, at least in part, by information provided with the processing of the plurality of images,
wherein a sorted food waste stream is generated with the removal of the non-biodegradable material from the sorting receptacle.

5. The automated food waste processing system of claim 4, wherein the actuator is a first actuator, the system further comprising a second actuator configured to articulate the sorting receptacle to discharge the sorted food waste stream from the sorting receptacle.

6. The automated food waste processing system of claim 1, wherein a liquid fertilizer is produced from the sorted food waste stream by the food waste processing system and output from the anaerobic digester,
wherein the food waste processing system includes a valve configured to dispense the liquid fertilizer, and
wherein the valve is accessible from a location outside of the enclosure.

7. The automated food waste processing system of claim 6, wherein a biogas is produced from the sorted food waste stream by the food waste processing system and output from the anaerobic digester, and wherein the food waste processing system includes an electrical generator configured to run on the biogas to generate electrical power employed by the food waste processing system.

8. An automated food waste processing system, the system comprising:
an enclosure secured to prevent unauthorized access to contents contained therein; and
a food waste processing system housed within the enclosure, the food waste processing system including:
an anaerobic digester having an input configured to receive a bio-degradable input stream and an output configured to discharge a liquid fertilizer generated by the anaerobic digester from the bio-degradable input stream;
a sorting receptacle configured to receive a food waste input stream for the anaerobic digester, the food waste input stream including food waste and non-biodegradable material;
an imaging system configured to automatically capture a plurality of images of the food waste input stream received by the sorting receptacle;
a processing system configured to automatically process the plurality of images to identify at least plastic waste and metal waste as the non-biodegradable material when included in the food waste input stream as received by the sorting receptacle, the plastic waste and the metal waste identified for removal from the food waste input stream;
a port accessible at an exterior of the enclosure, the port configured to allow personnel untrained in an operation of the food waste processing system to deposit the food waste input stream from a location outside of the enclosure for an automatic delivery to the sorting receptacle;
a fertilizer tank configured to hold the liquid fertilizer, the fertilizer tank including an input coupled to the output of the anaerobic digester and an output; and
a liquid fertilizer dispensing device coupled to the output of the fertilizer tank, the liquid fertilizer dispensing device accessible at the exterior of the enclosure, the liquid fertilizer dispensing device configured to allow personnel untrained in the operation of the food waste processing system to remove liquid fertilizer from the food waste processing system from a location outside of the enclosure.

9. The automated food waste processing system of claim 8, wherein the food waste processing system further comprises:
a sensor array included in the anaerobic digester;
a dosing tank with an input coupled to the sorting receptacle and an output coupled to the input of the anaerobic digester;
a pump including an input and an output, the pump configured to move the bio-degradable input stream through the automated food waste processing system;
a plurality of electrically operated valves coupled to the processing system;
a food waste disposal unit including an input coupled to the sorting receptacle and an output coupled to the input of the pump via a first electrically operated isolation valve included in the plurality of electrically operated valves, the food waste disposal configured to process the bio-degradable input stream supplied to the dosing tank;

a second electrically operated isolation valve included in the plurality of electrically operated valves and coupled to the output of the dosing tank and the input of the pump;

a third electrically operated isolation valve included in the plurality of electrically operated valves and coupled to the input of the anaerobic digester and the output of the pump;

a fourth electrically operated isolation valve coupled to the output of the anaerobic digester and the input of the pump; and a fifth electrically operated isolation valve coupled to the input of the fertilizer tank and the output of the pump, wherein the processing system is configured to automatically control an operation of the plurality of electrically operated valves to circulate the biodegradable input stream and the liquid fertilizer based on a status of a digestion process being performed by the anaerobic digester, the status determined using information provided by the sensor array.

10. The automated food waste processing system of claim 9, wherein the processing system is configured to automatically control the operation of the plurality of electrically operated valves to circulate the liquid fertilizer based on an elapsed time since a recirculation operation performed for the fertilizer tank.

11. A method of sorting a food waste input stream to generate an input stream to an anaerobic digester housed in an enclosure with other elements of a food waste processing system, the enclosure secured to prevent unauthorized access to contents contained therein, the enclosure including a plurality of exterior walls and a port accessible at an outside surface of an exterior wall included in the plurality of exterior walls, the port configured to allow personnel untrained in an operation of the food waste processing system to deposit food waste into the food waste input stream from a location outside of the enclosure, the method comprising:

receiving the food waste input stream at the port, the food waste providing the food waste input stream with a 95% or greater percentage by weight of biodegradable food waste;

automatically processing images of the food waste input stream using a trained neural network to identify non-biodegradable waste including identifying plastic waste and metal waste included in the food waste input stream;

automatically sorting the food waste input stream to remove the plastic waste and the metal waste based on information provided by the processing of the images;

automatically delivering the sorted food waste input stream to the anaerobic digester; and delivering liquid fertilizer produced with the anaerobic digester to a liquid fertilizer dispensing device accessible at the exterior of the enclosure, the liquid fertilizer dispensing device configured to allow personnel untrained in the operation of the food waste processing system to remove liquid fertilizer from the food waste processing system from a location outside of the enclosure.

12. The method of claim 11, further comprising automatically maintaining the food waste input stream in a first location for sorting for a predetermined amount of time.

13. The method of claim 12, further comprising:

performing a series of automated sorting operations to displace the food waste within the first location; and capturing a plurality of images associated with each of the automated sorting operations by:

capturing at least one image before each of the plurality of automated sorting operations; and capturing at least one image following each of the plurality of automated sorting operations.

* * * * *